(12) United States Patent
Thompson

(10) Patent No.: US 6,436,977 B1
(45) Date of Patent: Aug. 20, 2002

(54) DOSING REGIMENS FOR LASOFOXIFENE

(75) Inventor: David D. Thompson, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/656,273

(22) Filed: Sep. 6, 2000

Related U.S. Application Data

(60) Provisional application No. 60/156,652, filed on Sep. 29, 1999.

(51) Int. Cl.⁷ .................. A61K 31/425; A61K 31/42
(52) U.S. Cl. ........................ 514/367; 514/377
(58) Field of Search ................. 514/367, 377

(56) References Cited

U.S. PATENT DOCUMENTS

| | | | |
|---|---|---|---|
| 5,366,965 A | * | 11/1994 | Strein .................. 514/102 |
| 5,552,421 A | | 9/1996 | Lazer et al. |
| 6,043,026 A | * | 3/2000 | Patchett et al. .................. 435/4 |

FOREIGN PATENT DOCUMENTS

| | | |
|---|---|---|
| EP | 0792641 | 9/1997 |
| EP | 1004306 | 5/2000 |
| EP | 1086692 | 3/2001 |
| WO | WO 9621656 | 7/1996 |

* cited by examiner

*Primary Examiner*—Zohreh Fay
*Assistant Examiner*—Brian-Yong Kwon
(74) *Attorney, Agent, or Firm*—Peter C. Richardson; Gregg C. Benson; Todd M. Crissey

(57) ABSTRACT

Based on lasofoxifene's half-life and potency, the drug may be dosed once per week and achieve a similar effect as if given daily.

8 Claims, No Drawings

DOSING REGIMENS FOR LASOFOXIFENE

This application is filed claiming priority from co-pending Provisional Application No. 60/156,652 filed Sep. 29, 1999.

This invention relates to extended dosing regimens for the estrogen agonistlantagonist lasofoxifene, (−)-cis-6-phenyl-5-[4-(2-pyrrolidin-1 -yl-ethoxy)-phenyl]- 5,6,7,8-tetrahydronaphthalen-2-ol, D-tartrate.

BACKGROUND OF THE INVENTION

Lasofoxifene and related estrogen agonists/antagonists are disclosed in U.S. Pat. No. 5,552,421 (which is hereby incorporated by reference) as effective agents for treating or preventing diseases and conditions selected from obesity, breast cancer, osteoporosis, endometriosis and cardiovascular disease and hypercholesterolemia in male or female mammals and benign prostatic hypertrophy and prostatic carcinomas in male mammals.

This patent describes formulation and dosing procedures for the estrogen agonists/antagonists as follows:

The pharmaceutically acceptable acid addition salts of the compounds of this invention may be formed of the compound itself, or of any of its esters, and include the pharmaceutically acceptable salts which are often used in pharmaceutical chemistry. For example, salts may be formed with inorganic or organic acids such as hydrochloric acid, hydrobromic acid, hydroiodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferable with hydrochloric acid, citric acid, benzoic acid, maleic acid, acetic acid and propionic acid. It is usually preferred to administer a compound of this invention in the form of an acid addition salt, as it is customary in the administration of pharmaceuticals bearing a basic group such as the pyrrolidino ring.

The compounds of this invention, as discussed above, are very often administered in the form of acid addition salts. The salts are conveniently formed, as is usual in organic chemistry, by reacting the compound of this invention with a suitable acid, such as have been described above. The salts are quickly formed in high yields at moderate temperatures, and often are prepared by merely isolating the compound from a suitable acidic wash as the final step of the synthesis. The salt-forming acid is dissolved in an appropriate organic solvent, or aqueous organic solvent, such as an alcohol, ketone or ester. On the other hand, if the compound of this invention is desired in the free base form, it is isolated from a basic final wash step, according to the usual practice. A preferred technique for preparing hydrochlorides is to dissolve the free base in a suitable solvent and dry the solution thoroughly, as over molecular sieves, before bubbling hydrogen chloride gas through it.

The dose of a compound of this invention to be administered to a human is rather widely variable and subject to the judgement of the attending physician. It should be noted that it may be necessary to adjust the dose of a compound when it is administered in the form of a salt, such as a laureate, the salt forming moiety of which has an appreciable molecular weight. The general range of effective administration rates of the compounds is from about 0.05 mg/day to about 50 mg/day. A preferred rate range is from about 0.25 mg/day to 25 mg/day. Of course, it is often practical to administer the daily dose of compound in portions, at various hours of the day. However, in any given case, the amount of compound administered will depend on such factors as the solubility of the active component, the formulation used and the route of administration.

The route of administration of the compounds of this invention is not critical. The compounds are known to be absorbed from the alimentary tract, and so it is usually preferred to administer a compound orally for reasons of convenience. However, the compounds may equally effectively be administered percutaneously, or as suppositories for absorption by the rectum, if desired in a given instance.

The compounds of this invention are usually administered as pharmaceutical compositions, which are important and novel embodiments of the invention because of the presence of the compounds. All of the usual types of compositions may be used, including tablets, chewable tablets, capsules, solutions, parenteral solutions, troches, suppositories and suspensions. Compositions are formulated to contain a daily dose, or a convenient fraction of daily dose, in a dosage unit, which may be a single tablet or capsule or convenient volume of a liquid.

Any of the compounds may be readily formulated as tablets, capsules and the like; it is preferable to prepare solutions from water-soluble salts, such as the hydrochloride salt.

In general, all of the compositions are prepared according to methods known in pharmaceutical chemistry.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances, which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used as well as sodium lauryl sulfate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

When it is desired to administer a compound as a suppository, the typical bases may be used. Cocoa butter is a traditional suppository base, which may be modified by addition of waxes to raise its melting point slightly. Water-miscible suppository bases comprising, particularly, polyethylene glycols of various molecular weights are in wide use.

The effect of the compounds may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film, which resists dissolution for a predictable period of time. Even the parenteral preparations may be made long-acting, by dissolving or suspending the compound in oily or emulsified vehicles which allow it to disperse only slowly in the serum.

The active ingredient may be usually administered once to four times a day with a unit dosage of 0.1 mg to 50 mg in human patients, but the above dosage may be properly varied depending on the age, body weight and medical condition of the patient and the type of administration. A preferred dose is 0.25 mg in human patients. One dose per day is preferred."*

SUMMARY OF THE INVENTION

We have now found that contrary to the teaching of U.S. Pat. No. 5,552,421, that because of a long biological half-life, high potency and favorable safety factors it is possible to dose lasofoxifene once per a period of 7–30 days by oral delivery and achieve equivalent effect as if the drug were administered on a daily basis.

This invention provides a method of maintaining a safe, effective blood level of an estrogen agonist/antagonist for an extended period of time which comprises administering an oral dose which is of sufficient quantity to maintain said effective blood level for said extended period of time.

This invention also provides a method of maintaining a safe, effective blood level of an estrogen agonist/antagonist for an extended period of time which comprises administering an oral dose which is of sufficient quantity to maintain said effective blood level for said extended period of time wherein said estrogen agonist/antagonist is lasofoxifene.

This invention also provides a method of maintaining a safe, effective blood level of an estrogen agonist/antagonist for an extended period of time which comprises administering an oral dose which is of sufficient quantity to maintain said effective blood level for said extended period of time wherein said extended period of time is 7 days.

This invention also provides a method of maintaining a safe, effective blood level of an estrogen agonist/antagonist for an extended period of time which comprises administering an oral dose which is of sufficient quantity to maintain said effective blood level for said extended period of time wherein said sufficient quantity is 0.8 to 10.0 mg per dose.

DETAILED DESCRIPTION OF THE INVENTION

The prior art, for example U.S. Pat. No. 5,552,421, teaches that lasofoxifene and related compounds should be administered frequently in small doses. Doses as low as 0.1 mg four times per day are suggested for human patients.

We have now unexpectedly found that a single dose of 0.8 mg of lasofoxifene administered to healthy women resulted in an initial blood level of 0.7 ng/ml within a few hours. Levels declined slowly thereafter to a concentration of about 0.3 ng/ml after 168 hours (1 week). 0.3 ng/ml is considered to be a therapeutic effective dose.

Doses from 10 to 20 mg of lasofoxifene are acceptable. Such a dose would provide a therapeutically effective dose for up to 30 days. See Table 2.

EXAMPLE 1

A dose of 0.8 mg of lasofoxifene was administered to 12 healthy, postmenopausal women and blood samples were analyzed periodically as shown in Table 1.

A 1.0 ml sample of human plasma was analyzed for lasofoxifene according to CEDRA's Procedure TM-234 (CEDRA's address). Internal standard used for this procedure was a pentadeuterated lasofoxifene. The plasma sample containing lasofoxifene and the internal standard was extracted with MTBE. Following centrifugation, the organic layer was transferred to another tube and evaporated. An aliquot of the reconstituted sample extract was then injected onto a SCIEX API$^{III\text{-}PLUS}$ LC-MS-MS instrument equipped with a short ion exchange HPLC column. Peak areas of the m/z 414→97.9 daughter ion of lasofoxifene were measured against the peak areas of the mlz 419→97.9 daughter of the internal standard. Quantitation was performed using a 1/x weighted least squares regression line generated from spiked plasma calibration samples.

Plasma levels of lasofoxifene for 168 hours are shown in Table 1 below.

EXAMPLE 2

The procedure of Example 1 was repeated with a dose of 10-mg lasofoxifene administered to 8 healthy postmenopausal women. Plasma levels for lasofoxifene are shown for 672 hours in Table 2.

TABLE 1

Mean plasma concentrations of lasofoxifene following oral administration of a single dose of 0.8 mg to twelve healthy, post menopausal woman

| Hours after dosing | ng Lasofoxifene per ml plasma | Standard Deviation | Coefficient of variation |
| --- | --- | --- | --- |
| 0 | — | — | — |
| .5 | 0.13 | 0.10 | 77 |
| 1 | 0.32 | 0.09 | 28 |
| 2 | 0.37 | 0.06 | 15 |
| 4 | 0.46 | 0.10 | 23 |
| 8 | 0.72 | 0.13 | 19 |
| 12 | 0.73 | 0.14 | 19 |
| 24 | 0.64 | 0.11 | 18 |
| 48 | 0.56 | 0.10 | 17 |
| 72 | 0.49 | 0.08 | 16 |
| 120 | 0.40 | 0.07 | 18 |
| 168 | 0.34 | 0.10 | 29 |

TABLE 2

Mean plasma concentrations of lasofoxifene following oral administration of a single 10 mg dose to eight healthy, post menopausal woman

| Hours after dosing | na Lasofoxifene per ml plasma | Standard Deviation | Coefficient of variation |
| --- | --- | --- | --- |
| 0 | 0 | | |
| .5 | 2.33 | 1.19 | 51 |
| 1 | 4.42 | 0.86 | 19 |
| 2 | 5.64 | 1.36 | 24 |

TABLE 2-continued

Mean plasma concentrations of lasofoxifene following oral administration of a single 10 mg dose to eight healthy, post menopausal woman

| Hours after dosing | na Lasofoxifene per ml plasma | Standard Deviation | Coefficient of variation |
|---|---|---|---|
| 4 | 8.46 | 2.25 | 27 |
| 8 | 10.45 | 1.38 | 13 |
| 12 | 10.25 | 1.96 | 19 |
| 24 | 8.35 | 1.29 | 15 |
| 48 | 7.16 | 0.87 | 12 |
| 72 | 5.97 | 1.26 | 21 |
| 120 | 4.56 | 0.72 | 16 |
| 168 | 3.74 | 0.62 | 17 |
| 216 | 2.88 | 0.49 | 17 |
| 264 | 2.27 | 0.41 | 18 |
| 336 | 1.60 | 0.45 | 28 |
| 408 | 1.05 | 0.30 | 29 |
| 480 | 0.75 | 0.24 | 32 |
| 576 | 0.50 | 0.21 | 41 |
| 672 | 0.31 | 0.15 | 47 |

What is claimed is:

1. A method of administering (−)-cis-6-phenyl-5-[4-(2-pyrrolidin-1-yl-ethoxy)-phenyl]-5,6,7,8-tetrahydronaphthalen-2-ol or a pharmacologically acceptable salt thereof to a patient in need thereof, the method comprising administering a single dose, which dose results in a blood concentration of (−)-cis-6-phenyl-5-[4-(2-pyrrolidin-1-yl-ethoxy)-phenyl]-5,6,7,8-tetrahydronaphthalen-2-ol or a pharmacologically acceptable salt thereof of greater than about 0.3 ng/ml over an extended period of time wherein, the extended period of time is from about seven days to about thirty days.

2. The method of claim 1 wherein the single dose is about 0.8 to about 10.0 mg.

3. The method of claim 1 wherein the single dose is about 10.0 to about 20.0 mg.

4. The method of claim 1 wherein the single dose is about 0.8 mg and the extended period of time is about seven days.

5. The method of claim 1 wherein the single dose is about 10.0 mg and the extended period of time is about 30 days.

6. The method of claim 1 wherein the single dose is administered orally.

7. The method of claim 1 wherein the single dose is about 0.8 to about 20.0 mg and the extended period of time is about seven to about 30 days.

8. The method of claim 1 wherein the (−)-cis-6-phenyl-5-[4-(2-pyrrolidin-1-yl-ethoxy)-phenyl]-5,6,7,8-tetrahydronaphthalen-2-ol or a pharmacologically acceptable salt thereof is (−)-cis-6-phenyl-5-[4-(2-pyrrolidin-1-yl-ethoxy)-phenyl]-5,6,7,8-tetrahydronaphthalen-2-ol, D-tartrate.

* * * * *